United States Patent [19]
Co et al.

[11] Patent Number: 5,865,748
[45] Date of Patent: Feb. 2, 1999

[54] GUIDED DIRECTIONAL CORONARY ATHERECTOMY DISTAL LINEAR ENCODER

[75] Inventors: Fred Henrik Co, Santa Clara; Cheryl Swanson, Pacifica, both of Calif.

[73] Assignee: Guidant Corporation, Santa Clara, Calif.

[21] Appl. No.: 8,677

[22] Filed: Jan. 16, 1998

[51] Int. Cl.[6] ........................................ A61B 8/00
[52] U.S. Cl. ............................................ 600/439
[58] Field of Search ..................... 600/439, 459, 600/462, 463, 464, 466, 471, 461, 467; 606/159

[56] References Cited

U.S. PATENT DOCUMENTS

| | | |
|---|---|---|
| 4,448,200 | 5/1984 | Brooks et al. . |
| 4,587,972 | 5/1986 | Morantte, Jr. . |
| 4,794,931 | 1/1989 | Yock . |
| 4,870,953 | 10/1989 | DonMicheal et al. . |
| 4,887,605 | 12/1989 | Angelsen et al. . |
| 4,899,757 | 2/1990 | Pope, Jr. et al. . |
| 4,917,097 | 4/1990 | Proudian et al. . |
| 4,936,281 | 6/1990 | Stasz . |
| 4,947,852 | 8/1990 | Nassi et al. . |
| 4,947,864 | 8/1990 | Shockey et al. . |
| 4,976,691 | 12/1990 | Sahota . |
| 5,010,886 | 4/1991 | Passafaro et al. . |
| 5,038,789 | 8/1991 | Frazin . |
| 5,059,177 | 10/1991 | Towne et al. . |
| 5,090,958 | 2/1992 | Sahota . |
| 5,095,911 | 3/1992 | Pomeranz . |
| 5,109,859 | 5/1992 | Jenkins . |
| 5,109,861 | 5/1992 | Walinsky et al. . |
| 5,115,814 | 5/1992 | Griffith et al. . |
| 5,125,410 | 6/1992 | Misono et al. . |
| 5,131,397 | 7/1992 | Crowley . |
| 5,163,421 | 11/1992 | Bernsteiin et al. . |
| 5,163,432 | 11/1992 | Ueno et al. . |
| 5,186,177 | 2/1993 | O'Donnell et al. . |
| 5,190,045 | 3/1993 | Frazin . |
| 5,193,546 | 3/1993 | Shaknovich . |
| 5,269,793 | 12/1993 | Simpson . |
| 5,345,940 | 9/1994 | Seward et al. . |
| 5,368,035 | 11/1994 | Hamm et al. . |
| 5,443,456 | 8/1995 | Alliger et al. . |
| 5,451,785 | 9/1995 | Faris . |
| 5,464,016 | 11/1995 | Nicholas et al. . |
| 5,469,524 | 11/1995 | Esch et al. . |
| 5,493,109 | 2/1996 | Wei et al. . |
| 5,505,725 | 4/1996 | Samson . |
| 5,514,128 | 5/1996 | Hillsman et al. . |
| 5,520,189 | 5/1996 | Malinowski et al. . |
| 5,546,948 | 8/1996 | Hamm et al. . |
| 5,549,601 | 8/1996 | McIntyre et al. . |
| 5,558,093 | 9/1996 | Pomeranz . |
| 5,569,276 | 10/1996 | Jang et al. . |
| 5,660,180 | 8/1997 | Malinowski et al. .................. 600/439 |
| 5,715,825 | 2/1998 | Crowley .................................. 600/462 |

*Primary Examiner*—George Manuel
*Attorney, Agent, or Firm*—Peninsula IP Group; Douglas A. Chaikin

[57] ABSTRACT

Disclosed herein is a catheter device for use in a biological conduit having an encoder structure for indicating linear movement of the work element. The work element includes an ultrasonic transducer along a linear axis of the catheter. The catheter has a housing for insertion in the biological conduit. The transducer transmits ultrasonic pulses and receives echoes in response thereto for imaging an inside wall of the conduit. The housing has a window formed therein to image the conduit inside wall. An encoder structure adjacent an area of the window determines distal movement and travel direction of the transducer through the window area along a linear axis of the catheter housing.

17 Claims, 4 Drawing Sheets

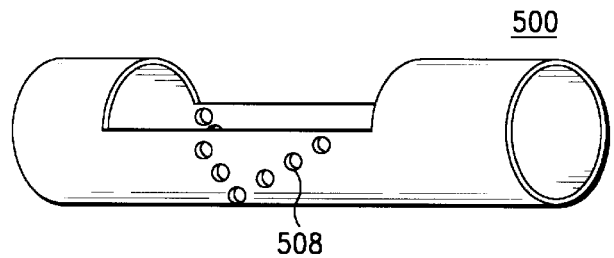
FIG.—5
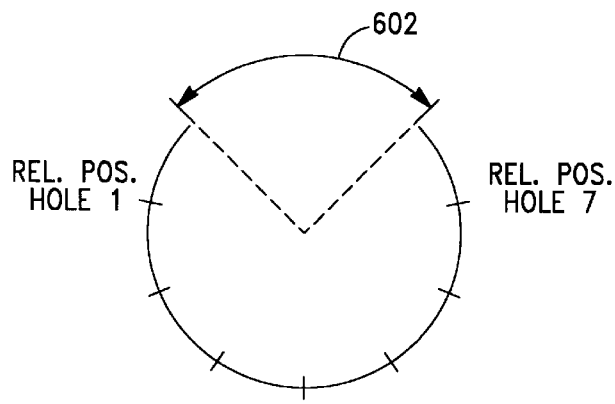
FIG.—6
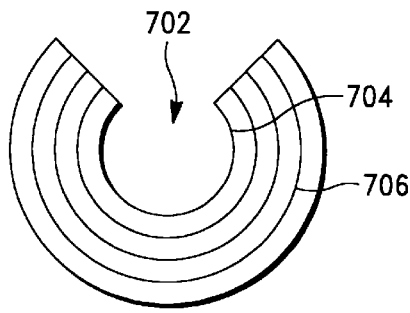
FIG.—7
(PRIOR ART)
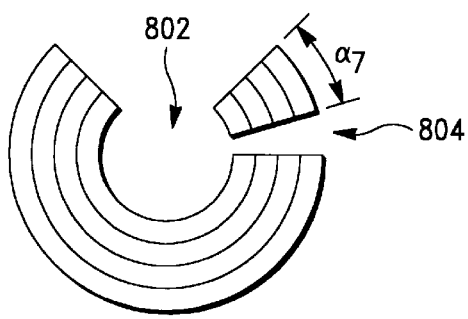
FIG.—8a
FIG.—8b

GUIDED DIRECTIONAL CORONARY ATHERECTOMY DISTAL LINEAR ENCODER

BACKGROUND OF THE INVENTION

1. Field Of The Invention

The invention relates to apparatus for intravascular imaging structures and in particular to mechanical guided directional coronary atherectomy catheters.

2. Description Of The Related Art

Ultrasonic imaging catheters, such as the one set forth in U.S. Pat. 5,193,546, which is incorporated herein by reference, are well known and have been developed to provide cross-sectional structural images of blood vessels and their lumens such as arteries in the vicinity of the heart. Operation of mechanically driven types of imaging catheters involves the insertion of a protective sheath which surrounds a long thin rotatable cable assembly with a transducer subassembly attached to its distal end into the blood vessel of interest. This complete assembly is the imaging catheter. The operator positions the contained transducer subassembly at a location within the blood vessel near the structures to be imaged as is illustrated in the aforementioned patent.

Ultrasonic images of the inside of the blood vessel are formed by using a sonar-like technique. In such assemblies, the transducer subassembly includes a transducer element rotatably mounted within the subassembly, generating a series of pulses which are transmitted outward from the transducer as the transducer is moved through 360° of rotation. The transmitted and echo ultrasonic pulses are substantially able to pass through the material of the sheath. Echo pulses reflected from structures inside the blood vessel lumen and the wall are received between transmitted pulses by the transducer and collected by control apparatus coupled with the rotating transducer and cable assembly within the sheath and displayed as a cross-sectional ultrasonic image of the inside of the blood vessel as set forth in U.S. Pat. 4,917,097, which is incorporated herein by reference.

A directional atherectomy catheter, such as is set forth in U.S. Pat. 4,794,931, which is incorporated herein by reference, is structurally similar to the imaging catheter. A cylindrical cutter is attached to the distal end of a long thin rotatable cable assembly which is contained within a sheath. Attached to the distal end of the sheath is a metallic cylindrical housing which surrounds and contains the cutter. The housing has a cut-out section, hereinafter referred to as the window, which exposes a cutting edge of the contained cutter. Opposite the window, a balloon is mounted on the housing. In use, a physician or operator uses fluoroscopy to position and direct the housing window toward an atheroma blocking blood flow in the lumen of the blood vessel. The balloon is inflated to press the housing window against the atheroma. The cutter is mechanically rotated via the long thin cable assembly and advanced distally through the housing to cut any atheroma pressed inside the housing window and pushes the cut atheroma, for storage, into a nosecone mounted on the distal end of the housing. An atherectomy procedure may require many cuts, controlled balloon inflations/deflations and positionings of the housing and window to remove and collect the desired amount of atheroma.

Guided directional atherectomy adds a transducer in, or near, the cutter to give the directional atherectomy catheter the ability to ultrasonically image the blood vessel. The ability to image the blood vessel allows a more precise and efficient catheter positioning and cutting of the atheroma.

The housing is generally constructed of a metallic material which will not substantially pass ultrasonic pulses. Therefore, the guided directional atherectomy catheter may only be used to image through the housing window. Generally, the window is cut in the housing surface at an angle of approximately 120° with respect to a center axis of the housing. Therefore, only a 120° section image view of the blood vessel adjacent to the housing window is obtained.

In a mechanically operated imaging or guided directional atherectomy catheter assembly, the transducer and cutter are located at the distal end of a long thin cable assembly generally comprised of a duplex spring assembly surrounding a coaxial cable extended through the sheath and connected at the proximal end to the control apparatus. The control apparatus rotates the proximal end of the cable assembly at a constant rate, typically 1800 RPM, and causes the transducer to generate an ultrasonic pulse at regular intervals, for example, approximately every 1.4° of rotation of the proximal end of the cable assembly. Thus, in the guided directional atherectomy catheter, approximately 85 transmit/receive cycles are generated as the transducer is transmitting pulses out of the housing window to create the 120° section image view of the blood vessel adjacent the housing window. The control apparatus operator can rotate the 120° housing window to view the entire inner surface of the blood vessel and move the transducer and cutter distally through the area of the housing window so as to remove the atheroma forced through the window by the catheter balloon.

A problem occurs in that the operator located at the proximal end of the catheter cable assembly is unaware of the precise position of the transducer and cutter within the catheter housing at the distal end of the cable assembly. Without the operator's knowledge, the transducer and cutter may be located at the rear, middle or front of the window area.

Accordingly, a need exists in the art for a guided directional coronary atherectomy catheter for use in determining the location and direction of travel of the to transducer and cutter in the window area of the distal ultrasound imaging catheter apparatus.

SUMMARY OF THE INVENTION

The foregoing problem and others that will be appreciated by those skilled in the art are solved by a guided directional coronary atherectomy ultrasound catheter apparatus having encoder structure formed thereon for indicating linear movement and travel direction of a transducer and cutter subassembly along a linear axis of the catheter apparatus.

It is an object of the invention to provide a guided directional coronary atherectomy ultrasound catheter having a housing mounting a rotating transducer and cutter subassembly positioned in a window formed in a housing surface for imaging a blood vessel and for removing a portion of a blood vessel atheroma. The catheter has a spiral encoder structure formed in the housing adjacent an area of the window for returning at least one echo pulse in response to transducer transmitted pulses at angles of rotation of the transducer and cutter subassembly defining linear movement and travel direction of the transducer and cutter subassembly along a rotational axis of the subassembly through the housing window area.

It is a further object of the invention to provide a guided directional coronary atherectomy ultrasound catheter, wherein the ultrasound catheter encoder spiral structure is formed as a plurality of indentations on the catheter housing and in an area adjacent the housing window at locations corresponding to angles of revolution of the catheter rotating transducer and cutter subassembly within the housing. The indentations are configured and positioned to return transducer pulse echoes defining the linear movement of the rotating transducer and cutter subassembly within the housing window along the rotational axis of the transducer and cutter subassembly.

It is a further object of the invention to provide a guided directional coronary atherectomy ultrasound catheter, wherein the ultrasound catheter encoder spiral structure is formed as a plurality of holes in the housing adjacent the housing window with each hole spaced apart from an adjacent hole. Each hole is positioned to define a predetermined angle of rotation of the transducer and cutter assembly and the plurality of holes defines linear movement and travel direction of the rotating transducer and cutter subassembly within the housing window along the rotational axis of the transducer and cutter subassembly.

It is yet another object of the invention to provide a guided directional coronary atherectomy ultrasound catheter, wherein the ultrasound catheter encoder spiral structure is formed as a channel in the housing adjacent the housing window and wherein the channel is configured to return echo pulses defining predetermined angles of rotation of the transducer and cutter subassembly in response to transducer transmitted pulses. The predefined angles each define a predetermined position of the rotating transducer and cutter subassembly within the housing window along the rotational axis of the transducer and cutter subassembly. When considered collectively, the predetermined angles provide an indication of the travel direction of the transducer and cutter subassembly.

In accordance with principles of the invention a guided directional coronary atherectomy ultrasound catheter for use with control Imaging apparatus comprises a transducer and cutter subassembly connected to a distal end of a cable used to couple the subassembly to the control imaging apparatus located at the proximal end of the cable. The transducer and cutter subassembly images an inside wall of the blood vessel and is controlled by an operator located at the control apparatus to remove a portion of an atheroma that may be blocking a flow of blood within the blood vessel.

A housing generally constructed of a material such as stainless steel is attached to the distal end of the cable for mounting the subassembly therein. The housing is configured to enable the control imaging apparatus by rotating and moving the cable to spin the subassembly about a rotational axis of the subassembly and to linearly move the subassembly along the subassembly rotational axis.

A window formed in a surface of the housing enables the transducer of the subassembly to transmit ultrasonic pulses under control of the control imaging apparatus toward the blood vessel wall.

Echo pulses returned from the blood vessel wall are received by the transducer and sent to the control imaging apparatus for imaging the blood vessel wall. The window may be rotated by means of the cable to provide a 360° view of the blood vessel wall and may be positioned to receive a portion of the atheroma to enable a cutter of the subassembly to remove the atheroma portion extending through the window.

An encoder structure formed in the housing adjacent an area of the window indicates linear movement of the transducer and cutter subassembly along the subassembly axis through the housing window area to the control imaging apparatus. The encoder is a spiral structure formed about the housing to extend from one end of the housing window to an opposite end thereof. The structure is configured to return at least one echo pulse in response to the transducer transmitted pulses to define at least one corresponding angle of revolution and linear movement of the transducer and cutter subassembly along the subassembly rotation axis.

In a first embodiment of the invention the encoder comprises a plurality of spiral indentations formed on the housing to have a depth so as to return a transducer pulse echo differing in time with respect to a transducer pulse echo returned from a wall of the housing. In another embodiment of the invention, the encoder may be a spiral conduit formed on the housing to have a depth so as to return a transducer pulse echo differing in time with respect to a transducer pulse echo returned from the housing wall. In other embodiments of the invention, the encoder may be formed as a spiral channel or a plurality of spiral holes in the housing with each hole spaced apart from an adjacent hole and positioned to define a predetermined angle of rotation of the subassembly and linear movement of the subassembly within the window area.

Another embodiment of the present invention is a catheter for use in a biological conduit, comprising:
  a housing having an open window area;
  a work element movably disposed within the housing, the work element having an imaging transducer mounted therein, the work element being attached to a distal end of a cable coupling the imaging transducer to an imaging apparatus; and
  a linear encoder formed in a spiral configuration in an area of the housing other than the open window area.

When transducer signals emitted in a direction of the encoder are returned to the transducer as encoder signal echoes, the encoder signal echoes are uniquely identifiable by the imaging apparatus, and provide an indicia of linear position and travel direction of the work element within the housing.

The linear encoder may be a plurality of equally spaced holes disposed in a spiral configuration, a spiral groove, a plurality of equally spaced indentations disposed in a spiral configuration, or a plurality of equally spaced protuberances disposed in a spiral configuration. From these encoder signal echoes, the imaging apparatus may generate a graphical representation of a position and travel direction of the work element within the housing in real time, by calculating an angle between the edges of the encoder signal echoes and an edge of the window area.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein:

FIG. 5 shows a perspective view of the housing of an atherectomy catheter incorporating the encoder structure according to the present invention.

FIG. 6 depicts an end view of the housing of an atherectomy catheter according to the present invention, showing the relative positions of the holes of one embodiment of the encoder structure according to the present invention.

FIG. 7 schematically shows an ultrasonic image through 360 degrees of rotation of a conventional ultrasonic imaging atherectomy catheter.

FIG. 8a shows an ultrasonic image produced with the catheter according to the present invention, showing the ultrasonic transducer sweeping past one hole of an embodiment of the encoder structure according to the present invention.

FIG. 8b is a computer generated graphical representation of an atherectomy catheter, and shows the transducer and cutter apparatus in a position corresponding to the hole illustrated in FIG. 8a.

FIG. 9b is a computer generated graphical representation of an atherectomy catheter, and shows the transducer and cutter apparatus in a position corresponding to the hole illustrated in FIG. 9a.

FIG. 10b is a computer generated graphical representation of an atherectomy catheter, and shows the transducer and cutter apparatus in a position corresponding to the hole illustrated in FIG. 10a.

DETAILED DESCRIPTION

Figure 1:
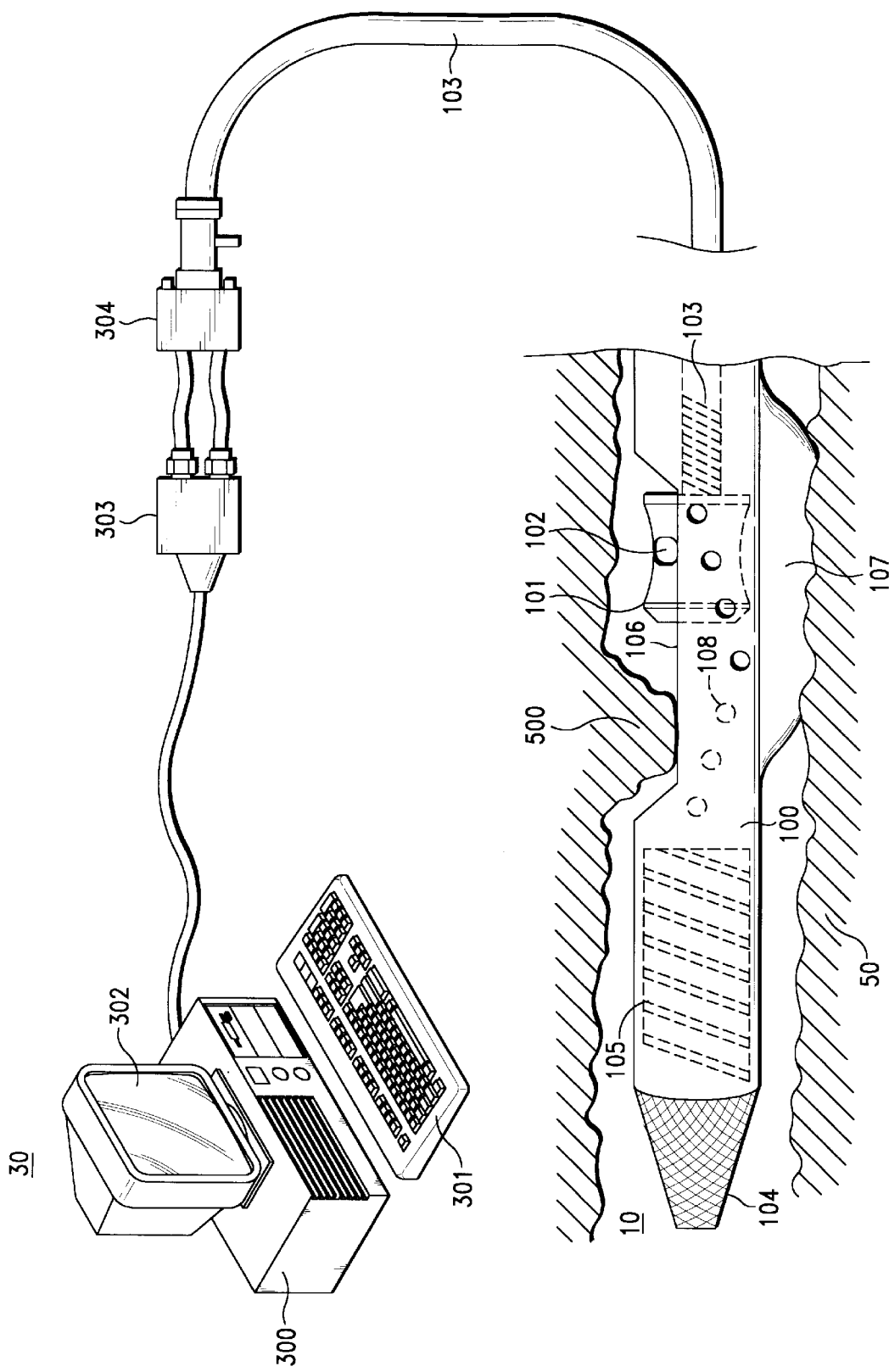
FIG. 1 is a view of mechanical guided directional coronary atherectomy catheter encoder apparatus in accordance with principles of the invention connected to control apparatus.
Figure 2:
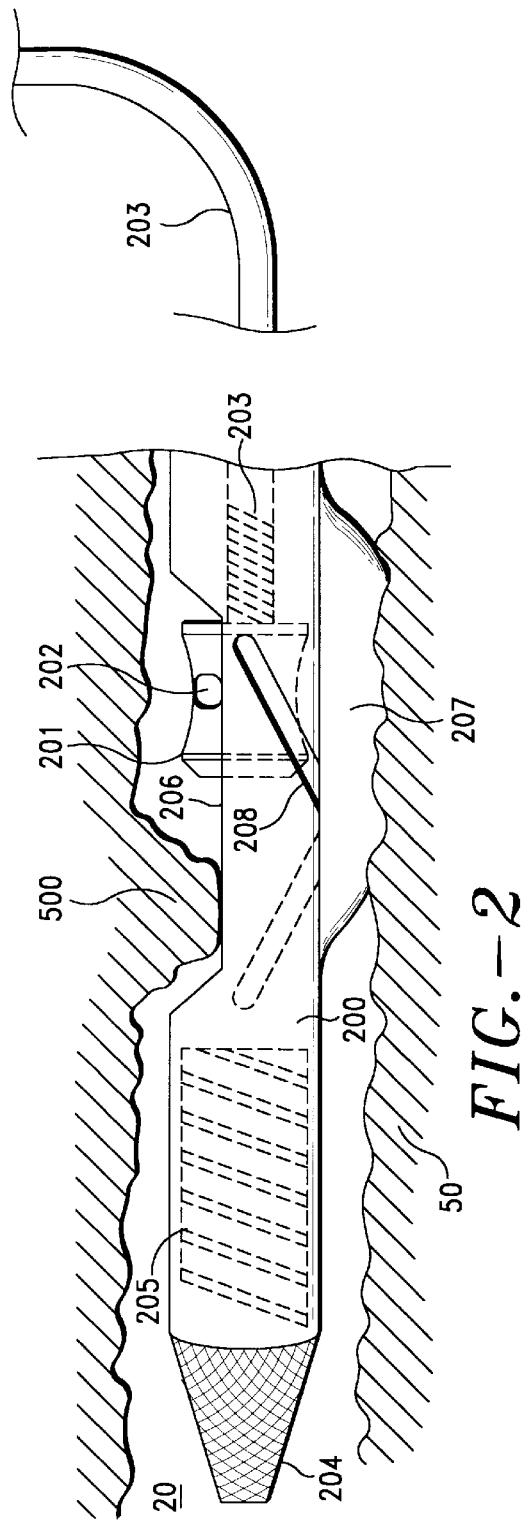
FIG. 2 illustrates another embodiment of the mechanical guided directional coronary atherectomy catheter apparatus of FIG. 1 in accordance with principles of the invention, and FIGS. 3 and 4 set forth a partial configuration of the directional coronary atherectomy catheter housing in the area of the window incorporating encoder structure of the invention.

Guided directional coronary atherectomy ultrasound catheters shown generally by the numerals 10 and 20, set forth in FIGS. 1 and 2 respectively of the drawing, are used with control imaging apparatus 30 to provide cross-sectional structural images of blood vessel 50 and to remove atheromas 500 that may be present therein, blocking the flow of blood in the blood vessel 50 and their lumens such as arteries in the vicinity of the heart. In operation a sheath, not shown, is generally inserted into the brachial or femoral artery of a patient and advanced in a well known manner through the arterial tree towards the heart. The catheters 10, 20, connected to a distal end of a cable assembly, hereinafter referred to as the cables 103, 203, are inserted into the proximal end of the sheath and guided through the arterial tree by fluoroscopy to a position in the blood vessel 50 determined by the attending physician or system operator located at the control imaging apparatus 30.

The Catheters 10, 20 each have a subassembly with a cylindrical cutter 101, 201, and a transducer 102, 202 attached to the distal end of the cables 103, 203, respectively, for imaging an inside wall of the blood vessel 50 and for enabling an operator, located at the control imaging apparatus 30 connected to the proximal end of the cables 103, 203, to remove a portion of the atheroma 500 blocking a flow of blood within the blood vessel 50. The transducers 102, 202, located within and on the surface of the cutters 101, 201, respectively, provide the guided directional atherectomy catheters 10, 20 the ability to ultrasonically image the inside wall of the blood vessel 50 and thereby allow a more precise and efficient positioning of the cutters 101, 201 and cutting of the atheroma 500.

Ultrasonic images of the inside wall of the blood vessel 50 are formed by using a sonar like technique. The transducers 102, 202 generate a series of ultrasonic pulses which are transmitted outward from the transducers 102, 202 as the transducers 102, 202 are moved through 360° of rotation. Echo pulses reflected from the wall of the blood vessel 50 and the atheroma 500 are received between transmitted pulses by the transducers 102, 202 and collected by the control imaging apparatus 30 to be displayed as a cross-sectional ultrasonic image of the blood vessel 50.

Attached to the distal end of the cables 103, 203 are cylindrical housings 100, 200 mounting the transducer 102, 202 and the cutter 101, 201 subassemblies. The housings 100, 200 are formed of a metallic material such as stainless steel and are configured for enabling the control imaging apparatus 30 to rotate the subassemblies about a rotational axis of the subassemblies and to linearly move the subassemblies along the subassembly rotational axis. Since the transducer emitted ultrasonic pulses do not pass through the wall of the metallic housings 100, 200, cut-out sections, hereinafter referred to as the windows 106, 206, are formed in the housing walls to expose the transducers 102, 202 and the cutters 101, 201 of the subassemblies rotatably and linearly mounted in the housings 100, 200. Typically, the housing windows 106, 206 are formed in the surface of the housings 100, 200 at an approximately 120° angle with respect to the housing's center axis. Therefore, only a 120° section image view of the wall of the blood vessel 50 is normally visible through the windows 106, 206. However, catheter interface unit 304, may be operated by the attending physician to rotate the housing windows 106, 206 to obtain a 360° cross-sectional view of the blood vessel 50. In use, the physician uses fluoroscopy to position and direct the catheters 10, 20 toward an atheroma 500 which is blocking blood flow in the blood vessel 50. A balloon, such as the balloons 107, 207 mounted on the bottom of the housings 100, 200, is inflated by the physician using a balloon port of the catheter interface unit 304 coupled with the proximal end of the cables 103, 203 to press the housing windows 106, 206 against the atheroma 500.

The catheter transducer and cutter subassemblies, mechanically rotated by the long thin cable assemblies 103, 203 attached to a motor located in proximal patient interface unit 303, are advanced by operation of the proximal catheter interface unit 304 linearly along the rotation axis of the subassemblies through a window area of the distal housings 100, 200. Rotation of the distal cutters 101, 201 cuts off the portion of the atheroma 500 pressed inside the housing windows 106, 206 and pushes the cut atheroma, for storage, into the nosecones 105, 205 which are mounted on the distal ends 104, 204 of the housings 100, 200. This procedure, referred to as an atherectomy procedure, may require many cuts, controlled balloon inflations/deflations and positionings of the housing and window to remove and collect the desired amount of the atheroma 500.

In an exemplary embodiment, the control imaging apparatus 30, FIG. 1, comprises a processing system such as the well known HP Sonos 100 Imaging System. It will be appreciated that other systems which are equivalent thereto are within the spirit and scope of this invention. Such processing systems are well known and need not be described in detail for an understanding of the invention. In general, the control imaging apparatus 30 has a central processing unit 300 coupled via a patient interface unit 303 and a catheter interface unit 304 to the proximal end of the cable assemblies 103, 203. A data input device such as a keyboard 301 or other type of data input device, is connected with a central processing unit 300 so that data such as words, numerals and control information may be exchanged with the central processor unit 300.

The patient Interface unit 303 has a motor or other type of apparatus for rotating the catheters 10, 20 via the cables 103, 203 and circuitry which generates an index pulse at predetermined degrees of rotation of the proximal end of the cable assemblies 103, 203 for enabling the distal transducers 102, 103 to generate an ultrasonic transmit pulse. The control imaging apparatus 30 may also have a video, CRT monitor, a display terminal 302 or printer device to display an image of the inside of the blood vessel 50 and the atheroma 500 from image echo pulses received from the distal catheter transducers 102, 202.

In operation, programs controlling operation of the catheters 10, 20 and the control apparatus 30 are stored in a program memory of the central processing unit 300 to control operation of the catheters 10, 20.

In the mechanically operated guided directional atherectomy catheters 10, 20, the transducers 102, 202 are located at the distal end of the long thin cables 103, 203 generally comprised of a duplex spring assembly surrounding a coaxial cable and connected at the proximal end via catheter and the patient interface units 304, 303 to the control imaging apparatus 30. The patient interface unit 303, under control of the control imaging apparatus 30, rotates the proximal end of the cables 103, 203, at a constant rate, typically 1800 RPM, to spin the catheter transducer 102, 202 and the cutter 101, 201 subassemblies. The spinning transducers 102, 202, transmit ultrasonic pulses out of the 120° housing window to create a section image view of the blood vessel 50 and the atheroma 500 adjacent to the housing windows 106, 206. The control apparatus operator can rotate the 120° housing window by using the catheter interface unit 304 to view the entire inner wall of the blood vessel 50 and move the rotating transducers 102, 202 and the cutters 101, 201 linearly along the rotational axis of the spinning subassemblies distally through the area of the housing windows 106, 206 so as to remove the portion of the atheroma 500 forced through the window by inflation of the catheter balloons 107, 207.

The housings 100, 200 are provided with encoder structures 108, 208 formed adjacent the windows 106, 206 for indicating distal movement of the transducers 102, 202 and the cutter 101, 201 subassemblies along a linear axis of the housings 100, 200 through the area of the windows 106, 206. Each encoder structure 108, 208, is configured as a spiral structure formed about the housings 100, 200 to extend along the center axis of the housings 100, 200 from one end of the housing windows 106, 206 to an opposite end thereof. During catheter operation, the spiral encoder structures 108, 208 return one of the echo pulses in response to transducer transmitted pulses to indicate angles of revolution, thus defining the linear movement of the transducers 102, 202 and the cutters 101, 201 through the area of the housing windows 106, 206.

When the transducers 102, 202 are positioned in the area of the windows 106, 206, transmitted pulses travel through the windows 106, 206 and are reflected as echo pulses from the walls of the blood vessel 50 and the atheroma 500. During the time from transmission to receipt of an echo pulse, the distance traveled by the pulses is twice the distance from the transducers 102, 202, to the wall of the blood vessel 50 and the atheroma 500. Since the metallic housings 100, 200 do not pass a transmitted pulse, rotation of the transducers 102, 202 outside the windows 106, 206 result in the pulses being returned from the housing walls after having traveled twice the short distance from the transducers 102, 202 to the inner wall of the housings 100, 200.

The spiral encoder structures 108, 208 are configured to return one of the transmitted and echo pulses that travel a different distance than those returned from the blood vessel 50 and the wall of the housings 100, 200. Thus, the spiral configuration of the encoder structures 108, 208 causes distinct echo pulses in response to transducer transmitted pulses that define angles of revolution and the linear movement of the transducers 102, 202 and the cutters 101, 201 subassemblies through the area of the housing windows 106, 206.

In one embodiment of the invention, the encoder structure 108, FIG. 1, is a plurality of spiral indentations formed on the housing wherein the depth or height of each indentation extending either outwardly or inwardly with respect to the surface of the housing 100 results in the return of a transducer pulse echo differing in time with respect to a transducer pulse echo returned from a wall of the housing 100.

In another embodiment, the encoder structure may be a spiral configuration of a series of protuberances formed on the wall of the housing 100 that results in the return of a transducer pulse echo differing in time with respect to a transducer pulse echo returned from a wall of the housing 100.

Figure 3:
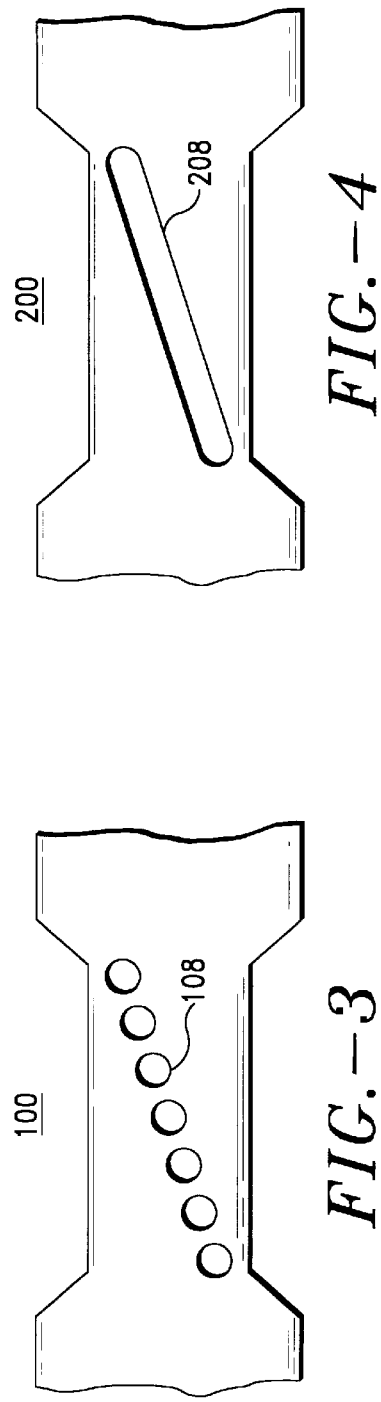

In yet another embodiment of the invention, FIG. 3, the encoder structure 108 may have a line of holes in the housing 100 such that when the housing 100 is configured as a cylinder, the holes form a spiral configuration along the center axis of the housing 100 wherein each hole results in the return of a transducer pulse echo from the blood vessel 50 that differs in time with respect to a transducer pulse echo returned from a wall of the housing 100. The plurality of indentations, protuberances or holes forming the spiral encoder structure 108 are each spaced apart from an adjacent indentation, protuberance and hole and are positioned to define a predetermined angle of rotation of the transducer 102. The predetermined angle defines the linear position and movement of the spinning transducer 102 and the cutter 101 subassembly along their axis of rotation.

Figure 4:
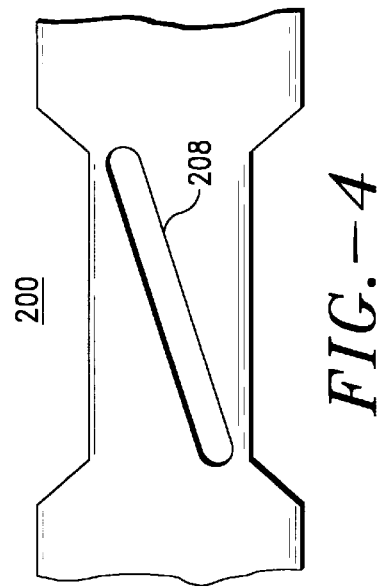

The spiral encoder structure 208, FIGS. 2 and 4, may also be a spiral conduit formed as a channel or protuberance on the housing 200 to have a depth or height so as to return a transducer pulse echo distinct in time with respect to a transducer pulse echo returned from a wall of the housing 200. Similarly, the encoder structure 208 may be a spiral channel formed in the housing 200 that is configured to return a transducer pulse echo from the blood vessel 50 to indicate a predetermined angle of rotation of the transducer 202 and the linear movement of the spinning transducer 202 and the cutter 201 within the area of the window 206.

An example of the operation of the guided directional coronary atherectomy catheter according to the present invention will now be explained, with reference to FIGS. 5–6, and 8a–10b.

FIG. 5 shows a schematic of a housing 500 incorporating an encoder structure 508. In the embodiment illustrated in FIG. 5, the encoder structure 508 comprises a plurality of holes formed in a spiral configuration through the wall of the housing 500. In the case illustrated in FIG. 5, seven equally spaced holes are shown, although a different number of holes may be used, depending on the positioning accuracy desired, or other considerations.

FIG. 6 depicts a cross-sectional diagram of the housing 500 of FIG. 5, showing the relative positions of the seven holes of the encoder structure of FIG. 5. The tissue viewing area, typically extending over a 120 degree arc, is referenced by numeral 602. The tissue viewing area corresponds to the window 106 of FIG. 1. As the holes of the encoder structure 508 are formed in a spiral, the relative positions of the holes 1–7 provide an indicia of the linear position and travel direction of the transducer and cutter assembly as it travels within the housing 500. In FIG. 6, hole number 7 can be said to occupy the 3 o'clock position, whereas hole number 1 can be said to occupy the 9 o'clock position, if the tick marks appearing on the figure were analogized to the hour marks on a standard analog clock face.

Prior art FIG. 7 schematically shows an ultrasonic image taken through 360 degrees of rotation, using a conventional guided directional coronary atherectomy catheter. Reference numeral 702 represents the tissue viewing area, and corresponds to the window area of a conventional housing. The true outline of the housing can be seen at numeral 704, whereas 706 graphically represents the ultrasonic ringing of the pulses sent from the transducer and the reflected echoes from the housing wall. As is apparent, no information can be extracted from such an image, other than from the tissue viewing area 702. Indeed, no positional or directional information of the transducer and cutter assembly can be inferred from the area exhibiting the ringing 706.

FIG. 8a shows an ultrasonic image produced from the catheter according to the present invention, as the transducer and cutter assembly 102, 101 of FIG. 1 is advanced to hole number 7. In FIG. 8a, the tissue viewing area is indicated at 802. However, FIG. 8a also shows an ultrasonic anomaly 804 at the 3 o'clock position. The anomaly 804 is produced as the transducer 102 of FIG. 1 is advanced to a position within the housing 100 of FIG. 1 corresponding to the 3 o'clock position. As was seen in FIG. 6, the 3 o'clock position corresponds to hole number 7 of the encoder structure 508 of FIG. 5. In that position, the ultrasonic pulse travels through hole number 7, and returns an echo from the arterial wall back through hole number 7, to be received by the transducer 102 of the cutter assembly 101. The anomaly 804, therefore, appears as a signal which is clearly distinct and uniquely identifiable from the ultrasonic ringing 706 of FIG. 7. This anomaly 804 could itself be used as a visual indicator of the linear position of the transducer 102 and cutter assembly 101 of FIG. 1. For example, the attending physician or operator could interpret an ultrasonic anomaly in the 3 o'clock position as an indication that the transducer 102 and cutter assembly 101 of FIG. 1 are in a proximal position within the housing 100 of FIG. 1. Alternatively, in a more sophisticated case, well known edge detection software could be employed to measure the angle $\alpha_7$, by counting the number of pulses between the edge of the tissue viewing area 802 and the leading edge of the anomaly 804. The angle $\alpha_7$ could then be used to produce a computer generated graphical representation of the atherectomy catheter, with the transducer and cutter assembly in a linear position within the housing corresponding to the measured angle $\alpha_7$, as shown in FIG. 8b. Indeed, FIG. 8b shows the transducer and cutter assembly in a proximal position within the housing, which position corresponds to the position of hole number 7 of FIG. 6. This provides the attending physician with an immediately intuitive graphical representation of the position of the transducer and cutter assembly of the catheter within the housing, in real time.

Figure 9A:
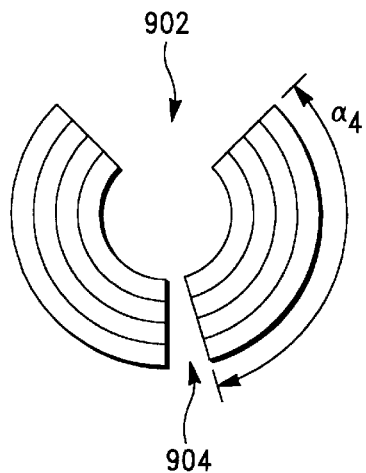
FIG. 9a shows an ultrasonic image produced with the catheter according to the present invention, showing the ultrasonic transducer sweeping past another hole of an embodiment of the encoder structure according to the present invention.
Figure 9B:
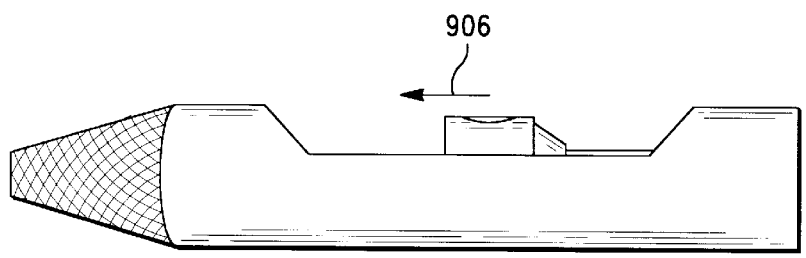

As the transducer 102 and cutter assembly 101 is advanced to hole number 4, for example, the location of the ultrasonic anomaly shifts accordingly. This situation is shown in FIG. 9a, wherein the ultrasonic anomaly is referenced by numeral 904. The anomaly 904 is in the 6 o'clock position, and corresponds to hole number 4. The location of ultrasonic anomaly 904 may be used by the attending physician directly to infer the position of the transducer 102, cutter subassembly 101 of FIG. 1. Alternatively edge detection software may measure the angle 4, in the same manner as angle $\alpha_7$ in FIG. 8a. From this information, a computer generated image of the atherectomy catheter may be formed, as shown in FIG. 9b. As shown in FIG. 9b, the linear position of the transducer 102, cutter 101 assembly corresponds to the relative position of hole number 4, as seen in FIG. 6. From FIG. 9b, the attending physician can immediately see that the transducer 102, cutter 101 assembly of FIG. 1 is approximately in the middle area of the housing 100 of FIG. 1.

Figure 10A:
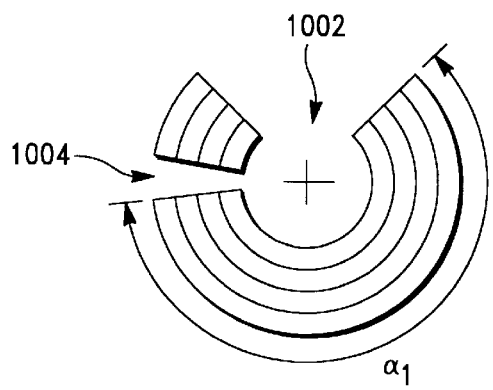
FIG. 10a shows an ultrasonic image produced with the catheter according to the present invention, showing the ultrasonic transducer sweeping past yet another hole of an embodiment of the encoder structure according to the present invention.
Figure 10B:
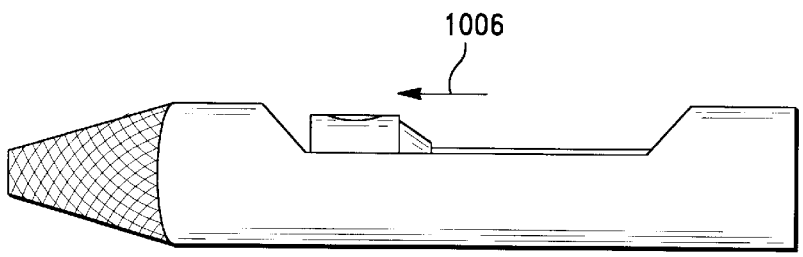

In like manner, FIGS. 10a and 10b show the condition wherein the ultrasonic anomaly 1004 is produced at a position corresponding to hole number 1 in FIG. 6. Edge detection software may be used to measure the angle $\alpha_1$, which angle places the ultrasonic anomaly 1004 at the 9 o'clock position. The graphical representation of the position of the catheter is shown in FIG. 10b, wherein the transducer 102, cutter 101 assembly is shown in the distal-most linear position within the housing 100 of FIG. 1.

The direction of travel of the transducer 102, cutter 101 assembly of FIG. 1 may be calculated by determining whether the transducer 102, cutter assembly 101 are advancing toward higher hole numbers, or toward lower hole numbers. For example, if the ultrasonic anomaly is observed at time $t_1$ at hole 7, and observed at a time $t_2$ later than time $t_1$ at hole 4, it may be inferred therefrom that the transducer 102, cutter 101 assembly is being advanced in the distal direction, as shown by arrows 906, 1006 in FIGS. 9b and 10b, respectively. Conversely, if the ultrasonic anomaly is observed at time $t_1$ at hole 1, and observed at a time $t_2$ later than time $t_1$ at hole 4, it may be inferred therefrom that the transducer 102, cutter 101 assembly is being retracted in the proximal direction.

It is apparent from the foregoing that the facility, economy and efficiency of guided directional coronary atherectomy catheter apparatus is improved by encoder structures for use in determining the location and direction of travel of a transducer and cutter subassembly within the housing window area of the distal ultrasound imaging catheter apparatus. It is also apparent that the distal linear encoder structure according to the present invention may also be used to determine the linear position and travel direction of intravenous ultrasonic (IVUS) imaging catheters, whose working element, typically an ultrasonic transducer, does not comprise a cutter element, without departing from the spirit of the invention.

While the foregoing detailed description has described several embodiments of the guided directional coronary atherectomy linear encoder in accordance with principles of the invention, it is to be understood that the above description is illustrative only and is not limiting of the disclosed invention. Particularly other configurations of encoder structures that return pulse echo information defining angular and linear movement of the distal catheter transducer and cutter subassembly within the catheter housing to proximal control apparatus are within the scope and spirit of this invention. Thus, the invention is to be limited only by the claims set forth below.

What is claimed is:

1. A guided directional coronary atherectomy ultrasound catheter, comprising:

an apparatus having a housing for insertion in a blood vessel with a subassembly positioned therein for transmitting and receiving ultrasonic pulses for imaging an inside wall of the blood vessel and for removing an atheroma blocking a flow of blood within the blood vessel and wherein the housing has a window formed therein with respect to the subassembly and wherein the housing has an encoder structure formed thereon adjacent an area of the window for indicating distal movement of the subassembly along a linear axis of the housing through the window area.

2. The guided directional coronary atherectomy ultrasound catheter, as set forth in claim 1, wherein the subassembly comprises:

a transducer and a cutter apparatus positioned within the housing to rotate about the axis of the housing and wherein the rotating transducer transmits ultrasonic pulses and receives echoes in response to the transmitted pulses for imaging the blood vessel wall and wherein linear movement of the transducer and cutter apparatus within the window area enables the rotating cutter to remove a portion of the atheroma extending through the housing window.

3. The guided directional coronary atherectomy ultrasound catheter as set forth in claim 2, wherein the encoder structure comprises:

a spiral structure formed about the housing adjacent the window and extending from one end of the window to an opposite end thereof, the spiral structure returning at least one echo pulse in response to the transducer transmitted pulses to indicate at least one corresponding angle of revolution, whereby the at least one corresponding angle of revolution provides an indicia of linear movement and direction of the transducer and cutter apparatus through the window area.

4. The guided directional coronary atherectomy ultrasound catheter as set forth in claim 3, wherein the encoder structure comprises:

a plurality of spiral indentations formed on the housing and wherein the depth and height of each indentation of the plurality of indentations is such as to return at least one transducer pulse echo differing in time with respect to a transducer pulse echo returned from a wall of the housing.

5. The guided directional coronary atherectomy ultrasound catheter as set forth in claim 3, wherein the encoder structure comprises:

a spiral conduit formed on the housing and wherein a configuration of the conduit is such as to return at least one transducer pulse echo differing in time with respect to a transducer pulse echo returned from a wall of the housing.

6. The guided directional coronary atherectomy ultrasound catheter as set forth in claim 3, wherein the encoder structure comprises:

a plurality of holes formed in the housing, each of the plurality of holes being spaced apart from an adjacent hole of the plurality of holes and wherein each hole is positioned to define a predetermined angle of rotation of the transducer and cutter apparatus.

7. The guided directional coronary atherectomy ultrasound catheter set forth in claim 3, wherein the encoder structure comprises:

a spiral channel formed in the housing, the channel being configured to enable a return of at least one transducer pulse echo defining at least one corresponding predetermined angle of rotation of the transducer and cutter apparatus.

8. A guided directional coronary atherectomy ultrasound catheter for use with control Imaging apparatus comprising:

a transducer and a cutter subassembly, the subassembly being connected to a distal end of a cable for coupling the subassembly to the control imaging apparatus located at the proximal end of the cable, for imaging an inside wall of a blood vessel and for removing a portion of an atheroma blocking a flow of blood within the blood vessel;

a housing attached to the distal end of the cable for mounting the subassembly therein, the housing enabling the control imaging apparatus to rotate the subassembly about a rotational axis of the subassembly and to linearly move the subassembly along the rotational axis;

a window formed in a surface of the housing wherein the window enables a transducer of the subassembly to transmit ultrasonic pulses under control of the control imaging apparatus toward the blood vessel inside wall and receive echo pulses returned therefrom for imaging the blood vessel inside wall, the window receiving a portion of the atheroma to enable a cutter of the subassembly to remove the atheroma portion extending through the window; and an encoder structure formed in the housing adjacent an area of the window for indicating linear movement of the transducer and cutter subassembly along the subassembly axis through the housing window area to the control imaging apparatus.

9. The guided directional coronary atherectomy ultrasound catheter as set forth in claim 8, wherein the encoder structure comprises:

a spiral structure formed around the housing adjacent the window and extending from one end of the housing window to an opposite end thereof and wherein the spiral structure returns at least one of the echo pulses in response to transducer transmitted pulses to define angles of revolution and indicia of linear movement and direction of the rotating transducer and cutter subassembly.

10. The guided directional coronary atherectomy ultrasound catheter as set forth in claim 9, wherein the encoder spiral structure comprises:

a plurality of indentations formed on the housing, each of the plurality of indentations corresponding to an individual one of the angles of revolution of the rotating transducer and cutter subassembly within the housing, the configuration of each indentation being such as to return at least one transducer pulse echo, the at least one transducer pulse echo providing indicia of the linear movement and travel direction of the rotating transducer and cutter subassembly along the rotational axis thereof.

11. The guided directional coronary atherectomy ultrasound catheter as set forth in claim 9, wherein the encoder spiral structure comprises:

a conduit formed on the housing adjacent the housing window, the conduit corresponding to the angles of revolution of the rotating transducer and cutter subassembly within the housing, the configuration of the conduit being such as to return at least one echo of transducer transmitted pulses defining the linear movement of the rotating transducer and cutter subassembly in the housing window area along the rotational axis of the subassembly.

12. The guided directional coronary atherectomy ultrasound catheter as set forth in claim 9, wherein the encoder spiral structure comprises:

a plurality of holes formed in the housing, each hole being spaced apart from an adjacent hole and positioned to define a predetermined angle of rotation of the transducer and cutter subassembly.

13. The guided directional coronary atherectomy ultrasound catheter as set forth in claim 9, wherein the encoder spiral structure, comprises: a channel formed in the housing, the channel being configured to return at least one echo pulse defining a predetermined angle of rotation of the transducer and cutter subassembly in response to a transducer transmitted pulse.

14. A housing for use with a guided directional coronary atherectomy ultrasound catheter to mount a rotating transducer and cutter subassembly connected to a distal end of a cable coupling the subassembly to control imaging apparatus located at the proximal end of the cable, the housing having a window formed in a surface thereof for enabling a transducer of the subassembly to transmit ultrasonic pulses under control of the control imaging apparatus for imaging an inside of a blood vessel and for receiving a portion of a blood vessel atheroma to enable a cutter of the subassembly to remove the atheroma portion extending through the window wherein the housing comprises:

a spiral encoder structure formed in the housing adjacent an area of the window for returning at least one echo pulse to the control imaging apparatus in response to the transducer transmitted pulses at angles of rotation of the transducer and the cutter subassembly, to provide indicia of linear movement and travel direction of the transducer and the cutter subassembly along a rotational axis of the subassembly through the housing window area.

15. A catheter for use in a biological conduit, comprising:

a housing having an open window area;

a work element movably disposed within the housing, the work element having an imaging transducer mounted therein, the work element being attached to a distal end of a cable coupling the imaging transducer to an imaging apparatus; and a linear encoder formed in a spiral configuration in an area of the housing other than the open window area, whereby, transducer signals emitted toward the encoder and returned to the transducer as encoder signal echoes are uniquely identifiable by the imaging apparatus, and provide an indicia of linear position and travel direction of the work element within the housing.

16. A catheter according to claim 15, wherein the linear encoder comprises one of:

a plurality of equally spaced holes disposed in a spiral configuration, a spiral groove, a plurality of equally spaced indentations disposed in a spiral configuration, and a plurality of equally spaced protuberances disposed in a spiral configuration.

17. A catheter according to claim 15, wherein the imaging apparatus generates a graphical representation of a position and travel direction of the work element within the housing from the encoder echoes, in real time, by calculating an angle between the edges of the encoder echoes and an edge of the window area.

* * * * *